United States Patent [19]

VandenBerg

[11] Patent Number: Plant 7,346

[45] Date of Patent: Oct. 2, 1990

[54] CHRYSANTHEMUM PLANT NAMED PASADENA

[75] Inventor: Cornelis P. VandenBerg, Salinas, Calif.

[73] Assignee: Yoder Brothers, Inc., Barberton, Ohio

[21] Appl. No.: 388,896

[22] Filed: Aug. 2, 1989

[51] Int. Cl.[5] ..... A01H 5/00

[52] U.S. Cl. ..... Plt./74

[58] Field of Search ..... Plt./74

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Pasadena particularly characterized by its flat capitulum form, spoon daisy capitulum type, dark red-purple ray floret color, diameter across face of capitulum of up to 14 cm at maturity when grown as a pinched disbud pot mum, uniform eight week photoperiodic flowering response to short days, short plant height when grown as a pinched pot mum, and spreading branching pattern.

3 Drawing Sheets

The present invention comprises a new and distinct cultivar of Chrysanthemum, botanically known as *Dendranthema grandiflora,* and referred to by the cultivar name Pasadena.

Pasadena, identified as 84-Y91002, was originated from a cross made by Cornelis P. VandenBerg in a controlled breeding program in Salinas, Calif., in 1984.

The female parent of Pasadena was an unnamed seedling identified as 84-418005. The male parent of Pasadena was an unnamed seedling identified as 81-C53001.

Pasadena was discovered and selected as one flowering plant within the progeny of the stated cross by Cornelis P. VandenBerg in November of 1984, in a controlled environment in Salinas, Calif.

The first act of asexual reproduction of Pasadena was accomplished when vegetative cuttings were taken from the initial selection in January of 1985 in a controlled environment in Salinas, Calif., by technicians working under formulations established and supervised by Cornelis P. VandenBerg.

Horticultural examination of controlled flowering of successive plantings has shown that the unique combination of characteristics as herein disclosed for Pasadena are firmly fixed and are retained through successive generations of asexual reproduction.

Pasadena has not been observed under all possible environmental conditions. The phenotype may vary significantly with variations in environment such as temperature, light intensity and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Pasadena, which, in combination, distinguish this Chrysanthemum as a new and distinct cultivar:

1. Flat capitulum form.
2. Spoon daisy capitulum type.
3. Dark red-purple ray floret color.
4. Diameter across face of capitulum up to 14 cm at maturity, when grown as a pinched disbud pot mum.
5. Uniform eight week photoperiodic flowering response to short days.

6. Short plant height, requiring 7 to 14 long days after pinch prior to short days and 0 to 1 application of 2500 ppm B-9 SP to attain a flowered plant height of 25 to 35 cm for year-round flowerings when grown as a pinched pot mum in a 15 cm pot.
7. Branching pattern is spreading.

The accompanying photographic drawings show typical inflorescence and leaf characteristics of Pasadena, with the colors being as nearly true as possible with illustrations of this type. Sheet 1 is a color photograph of Pasadena grown as a pinched disbud pot mum grown in a 15 cm pot. Sheet 2 is a black and white photograph of three views of the inflorescence of Pasadena. Sheet 3 is a black and white photograph showing the upper and under sides of the leaves of Pasadena at three stages of development (mature, intermediate and immature).

Of the commercial cultivars known to the inventor, the most similar in comparison to Pasadena is Neoga, disclosed in U.S. Plant Pat. No. 6,312. Reference is made to attached Chart A, which compares certain characteristics of Pasadena to the same characteristics of Neoga.

Similar traits are capitulum form and type, branching pattern, and flowering response. The ray floret color of Pasadena is a very dark red-purple, compared to the light purple color of Neoga. The spoon length of Pasadena is shorter than that of Neoga. Pasadena has a slightly larger flower and a shorter plant habit than Neoga.

In the following description color references are made to The Royal Horticultural Society Colour Chart. The color values were determined on plant material grown as a pinched disbud pot mum in Salinas, Calif. on Mar. 28, 1989.

Classification:

*Botanical.*—*Dendranthema grandiflora* cv Pasadena.

*Commercial.*—Spoon daisy disbud pot mum.

INFLORESCENCE

A. Capitulum:

*Form.*—Flat.

*Type.*—Spoon daisy.

*Diameter across face.*—Up to 14 cm at maturity.

B. Corolla of ray florets:

*Color (general tonality from a distance of three meters).*—Dark red-purple.

*Color of spoon tips.*—59B.

*Color of tubes.*—186C.

*Shape.*—Base tubular. Distal portion open, flattened and spoon-like. The length of the flattened spoon comprises up to 40% of the total petal length.

C. Corolla of disc florets:

*Color (mature).*—7A.

*Color (immature).*—144A to 144B.

D. Reproductive organs:

*Androecium.*—Present on disc florets only; no pollen.

*Gynoecium.*—Present on both ray and disc florets.

PLANT

A. General appearance:

*Height.*—Short; 25 to 35 cm as a pinched disbud pot mum with 7 to 14 long days after pinch prior to short days and 1 application of 2500 ppm B-9 SP.

*Branching pattern.*—Spreading.

B. Foliage:

*Color (upper surface).*—147A.

*Color (under surface).*—147B.

*Shape.*—Lobed and slightly serrated.

CHART A
COMPARISON OF PASADENA AND NEOGA

| CULTIVAR | PASADENA | NEOGA |
|---|---|---|
| Ray Floret Color | Dark red-purple | Purple |
| Capitulum Form and Type | Flat Spoon Daisy | Flat Spoon Daisy |
| Branching Pattern | Spreading | Spreading |
| Diameter Across Face of Capitulum | Up to 14 cm | Up to 12 cm |
| Plant Height | Short | Medium |
| Controlled Response | 8 weeks | 8 weeks |

Comparison Made of Plants Grown
As Pinched Disbud Pot Mums
In Salinas, California

I claim:

1. A new and distinct Chrysanthemum plant named Pasadena, as described and illustrated.

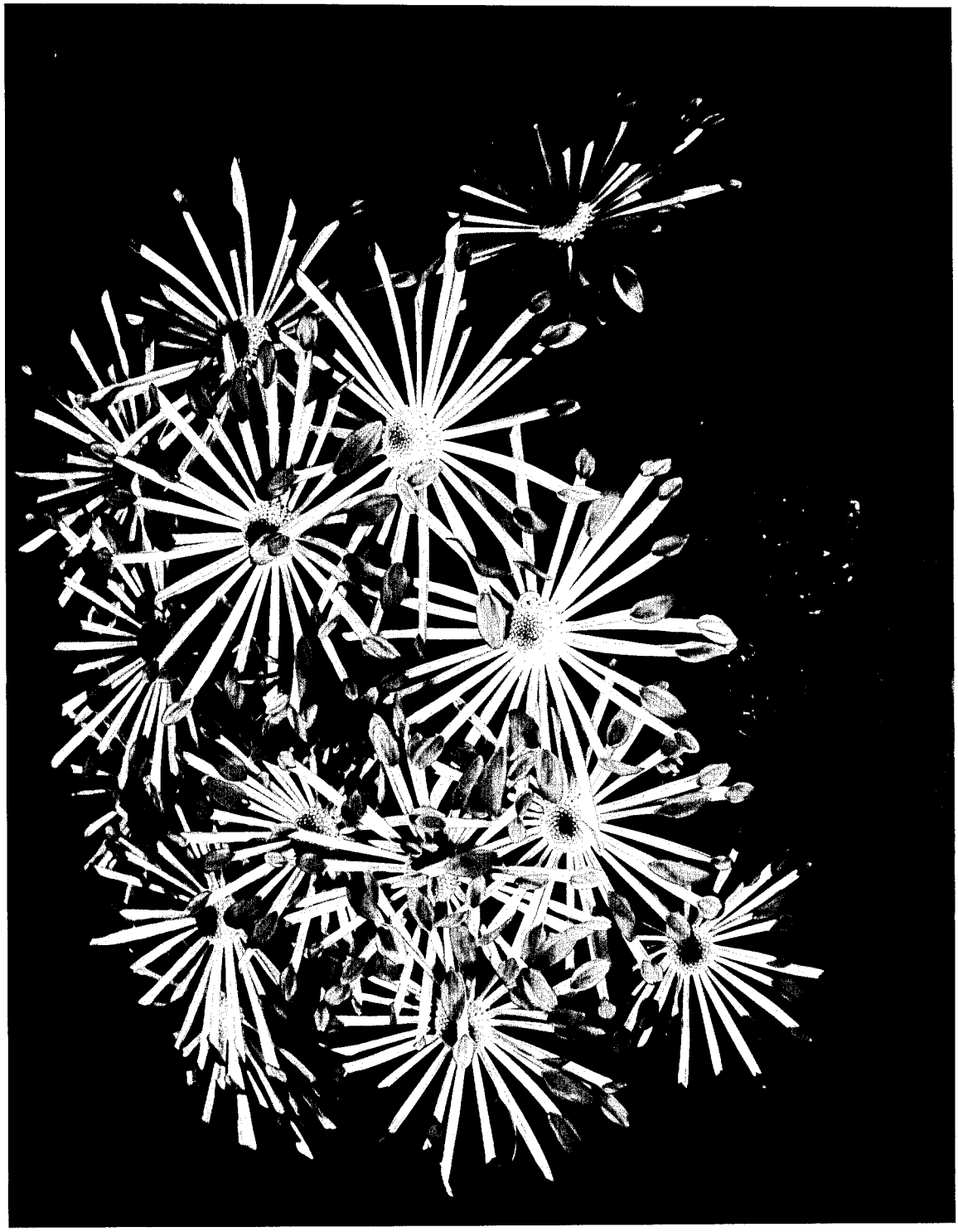

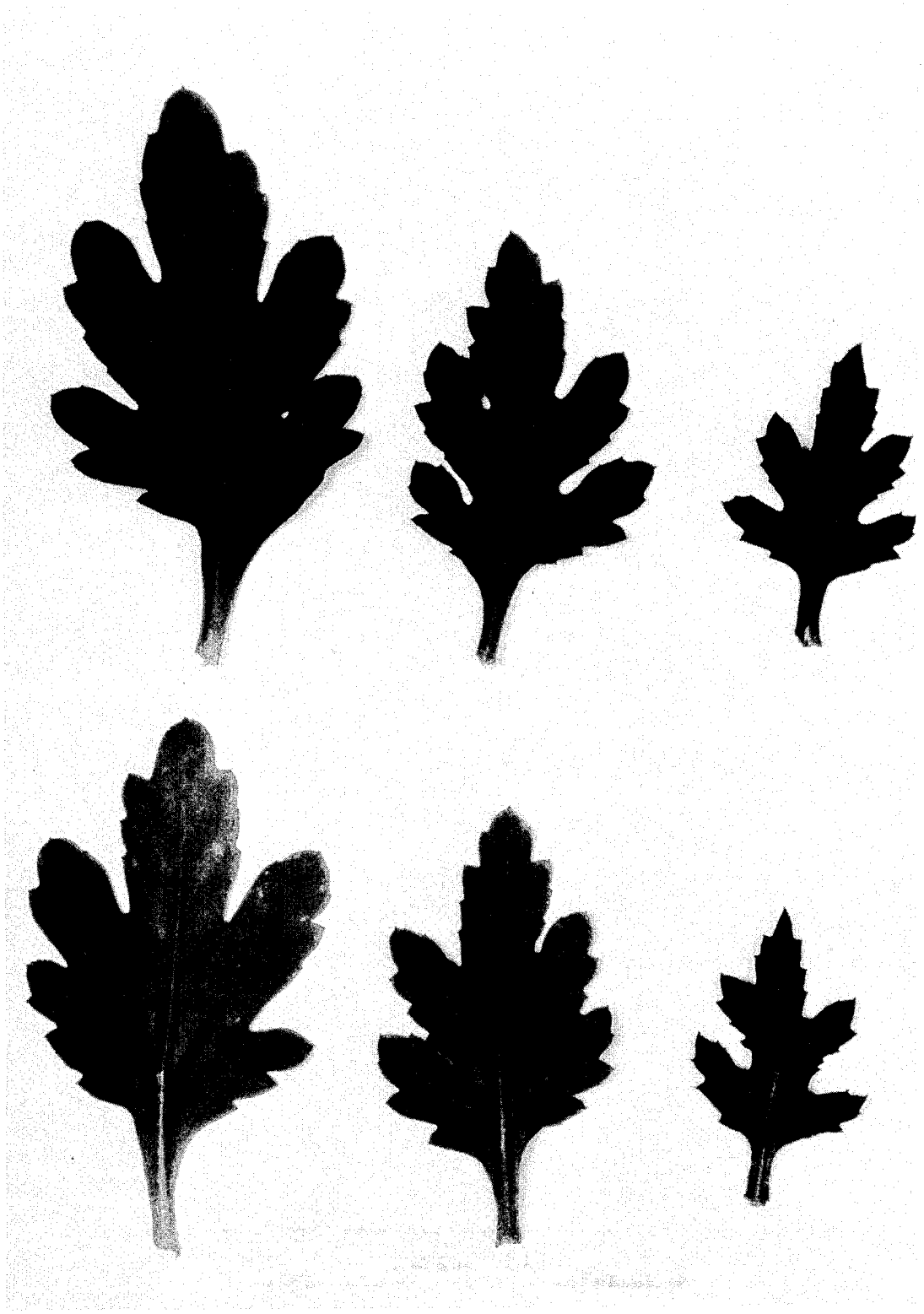

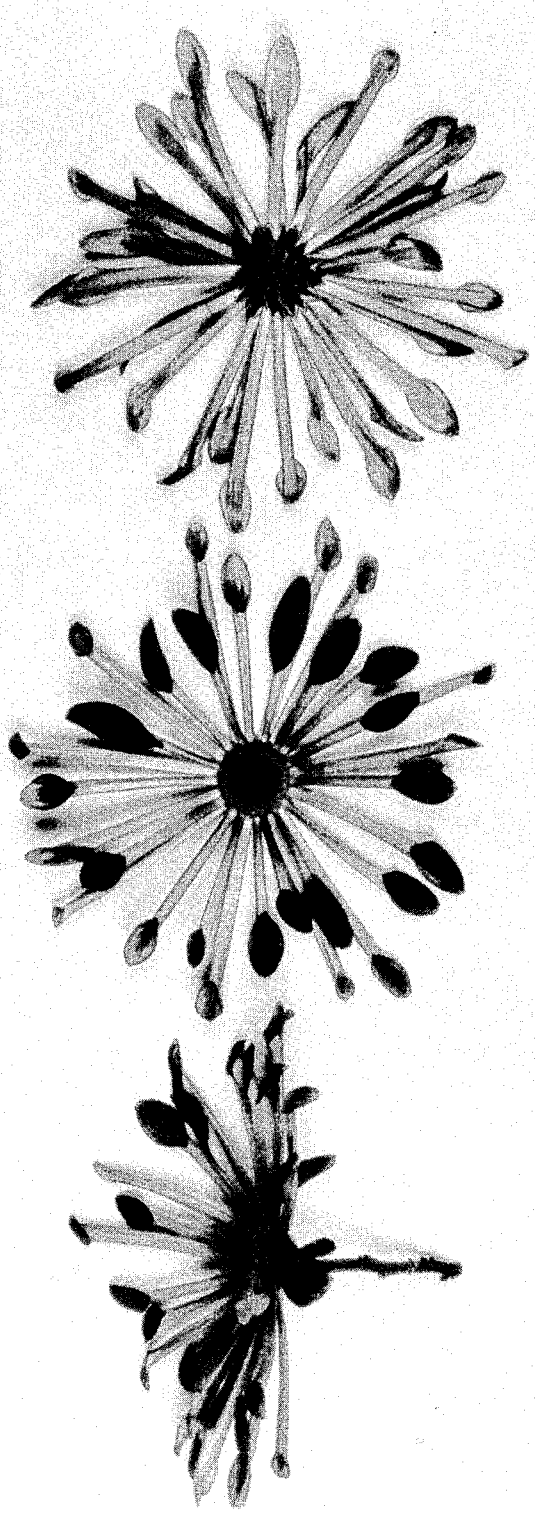

* * * * *